United States Patent
Hoshino et al.

(10) Patent No.: US 7,060,645 B2
(45) Date of Patent: Jun. 13, 2006

(54) METHOD FOR MANUFACTURING ZEOLITE AND METHOD FOR MANUFACTURING ε-CAPROLACTAM

(75) Inventors: Masahiro Hoshino, Niihama (JP); Masaru Kitamura, Niihama (JP); Keisuke Sugita, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/165,538

(22) Filed: Jun. 24, 2005

(65) Prior Publication Data

US 2006/0004194 A1    Jan. 5, 2006

(30) Foreign Application Priority Data

Jun. 30, 2004   (JP) ............................. 2004-193265

(51) Int. Cl.
*B01J 29/40* (2006.01)
*C07D 201/04* (2006.01)

(52) U.S. Cl. ........................... 502/86; 502/60; 502/77; 502/85; 423/700; 540/536

(58) Field of Classification Search ................ 423/700, 423/DIG. 22, DIG. 29, DIG. 34; 502/60, 502/77, 85, 86; 540/536

See application file for complete search history.

(56) References Cited

U.S. PATENT DOCUMENTS

| 4,678,766 | A | * | 7/1987 | Rosinski ...................... 502/86 |
| 5,139,761 | A | * | 8/1992 | Nair et al. ................... 423/704 |
| 5,212,302 | A | * | 5/1993 | Kitamura et al. ........... 540/536 |
| 6,071,844 | A | * | 6/2000 | Hoelderich et al. ........... 502/77 |
| 2003/0165425 | A1 | * | 9/2003 | Sugita et al. ................ 423/704 |

FOREIGN PATENT DOCUMENTS

| EP | 0 494 535 A1 | | 7/1992 |
| EP | 1 065 167 A1 | | 1/2001 |
| EP | 1 352 902 A1 | | 10/2003 |
| JP | 2-250866 | | 10/1990 |
| JP | 2-275850 | | 11/1990 |
| JP | 5-170732 | | 7/1993 |
| JP | 05170732 A | * | 7/1993 |
| JP | 2-201966 | | 8/1993 |
| JP | 5-201965 | | 8/1993 |
| JP | 6-107627 | | 4/1994 |
| JP | 2003176125 A | * | 6/2003 |
| JP | 2004-75518 | | 3/2004 |

* cited by examiner

*Primary Examiner*—David Sample
(74) *Attorney, Agent, or Firm*—Foley & Lardner LLP

(57) ABSTRACT

The present invention provides a method for manufacturing a zeolite comprising following steps of:
(1): calcining crystals obtained by hydrothermal synthesis reaction of a silicon compound;
(2): contact treating a calcined product obtained by the step (1) with an aqueous solution including an amine and/or a quaternary ammonium compound;
(3): calcining a treated product obtained by the step (2); and
(4): contact treating the calcined product obtained by the step (3) with an aqueous solution including ammonia and/or an ammonium salt.

According to the present invention, a method is also provided wherein ε-caprolactam is manufactured by Beckmann rearrangement reaction of cyclohexanone oxime in a gaseous phase in the presence of the zeolite manufactured by the above-described method.

5 Claims, No Drawings

METHOD FOR MANUFACTURING ZEOLITE AND METHOD FOR MANUFACTURING ε-CAPROLACTAM

BACKGROUND OF THE INVENTION

1. Field of the Invention

The present invention relates to a method for manufacturing a zeolite. Moreover, the present invention also relates to a method for manufacturing ε-caprolactam from cyclohexanone oxim using the zeolite as a catalyst.

2. Prior Art

Conventionally, a method of Beckmann rearrangement reaction of cyclohexanone oxime in a gaseous phase using zeolites as a catalyst has been known as one of methods for manufacturing ε-caprolactam. As a method for manufacturing such zeolites having good activity as a catalyst, for example, Japanese Patent Laid-Open Publication No. 5-170732 proposes a method wherein after calcination of crystals obtained by hydrothermal synthesis reaction of a silicon compound, the crystals are subjected to contact treatment with an aqueous solution of a basic material selected from ammonia, lower alkylamines, allylamines, and alkyl ammonium hydroxides, and an ammonium salt, or with aqueous ammonia. Moreover, Japanese Patent Laid-Open Publication No. 2004-75518 proposes a method wherein crystals obtained by hydrothermal synthesis reaction of a silicon compound are calcined, and subsequently is subjected to contact treatment in an aqueous solution of a quaternary ammonium salt and ammonia.

SUMMARY OF THE INVENTION

An object of the present invention is to provide a method for manufacturing a zeolite having further excellent catalytic activity. Another object of the present invention is to provide a method for manufacturing ε-caprolactam with sufficient productivity by making cyclohexanone oxime to react at a high conversion using the obtained zeolite as a catalyst.

The present invention provides a method for manufacturing a zeolite comprising following steps of:

(1): calcining crystals obtained by hydrothermal synthesis reaction of a silicon compound;
(2): contact treating a calcined product obtained by the step (1) with an aqueous solution including an amine and/or a quaternary ammonium compound;
(3): calcining a treated product obtained by the step (2); and
(4): contact treating the calcined product obtained by the step (3) with an aqueous solution including ammonia and/or an ammonium salt.

According to the present invention, a method is also provided wherein ε-caprolactam is manufactured by Beckmann rearrangement reaction of cyclohexanone oxime in a gaseous phase in the presence of the zeolite manufactured by the above-described method.

According to the present invention, zeolites having outstanding catalytic activity can be manufactured. Furthermore, using thus obtained zeolite as a catalyst Beckmann rearrangement reaction of cyclohexanone oxime in a gaseous phase enables a reaction of cyclohexanone oxime at a high conversion to produce ε-caprolactam with sufficient productivity.

DETAILED DESCRIPTION OF THE INVENTION

A zeolite, as a target of the present invention, includes silicon and oxygen as elements constituting a skeleton thereof and may be crystalline silica having a skeleton substantially constituted with silicon and oxygen, or may be crystalline metallosilicate further including other elements as elements constituting a skeleton thereof. In the case of crystalline metallosilicate, other elements that may exist in addition to silicon and oxygen, for example, include Be, B, Al, Ti, V, Cr, Fe, Co, Ni, Cu, Zn, Ga, Ge, Zr, Nb, Sb, La, Hf, Bi, etc., and two or more of them may be included if necessary.

Although various structures are known for the above-mentioned zeolite, a zeolite having a pentasil type structure is especially preferable, and a zeolite having an MFI structure is more preferable.

In the present invention, manufacture of the zeolite is performed by a method comprising following steps (1) to (4):

(1): calcining crystals obtained by hydrothermal synthesis reaction of a silicon compound;
(2): contact treating a calcined product obtained in the step (1) with an aqueous solution including an amine and/or a quaternary ammonium compound;
(3): calcining a treated product obtained in the step (2); and
(4): contact treating the calcined article obtained in the step (3) with an aqueous solution including ammonia and/or an ammonium salt. The series of steps enable manufacture of a zeolite having outstanding catalytic activity.

Publicly known methods are appropriately employable as a hydrothermal synthesis reaction of a silicon compound, and especially, a method of mixing a silicon compound with water and tetraalkyl ammonium hydroxide, and then heat-treating this mixed liquor is suitably adopted. As a silicon compound, orthosilicic acid tetra-alkyl esters like orthosilicic acid tetra-methyl ester, orthosilicic acid tetra-ethyl ester, orthosilicic acid tetra-propyl ester, and orthosilicic acid tetra-butyl ester may preferably used. Tetraalkylammonium hydroxide can work as a structure directing agent and/or a base, and tetramethylammonium hydroxide and tetrapropylammonium hydroxide may preferably be used.

When preparing the mixed liquor, as raw materials to be mixed, if necessary, components other than the silicon compound, water, and tetraalkylammonium hydroxide may be used. For example, in order to adjust hydroxide ion concentration in the mixed liquor, basic compounds like sodium hydroxide or potassium hydroxide may be mixed therein. Moreover, in order to adjust tetraalkylammonium ion concentration in the mixed liquor, tetraalkylammonium salts like tetraalkylammonium bromide may be mixed therein.

A molar ratio of water to silicon in the mixed liquor is usually adjusted to 5 to 100, preferably to 10 to 60. A molar ratio of tetraalkyl ammonium ion to silicon is usually adjusted to 0.1 to 0.6, preferably to 0.2 to 0.5. A molar ratio of hydroxide ion to silicon is usually adjusted to 0.1 to 0.6, preferably to 0.2 to 0.5. Furthermore, in the case of crystalline metallosilicate previously mentioned, compounds including elements other than silicon and oxygen are mixed with, and a molar ratio of silicon to the elements other than silicon and oxygen in the mixed liquor is adjusted to preferably not less than 5, and more preferably not less than 500.

A heat treatment temperature for subjecting the mixed liquor to hydrothermal synthesis reaction is usually 80 to 160° C., and a heat treatment period is usually 1 to 200 hours.

Crystals are separated from a reaction mixture obtained by the hydrothermal synthesis reaction using methods such as concentration, filtration, etc., then subjected to treatment of drying etc. if necessary, and then calcined [Step (1)]. This calcination step is usually suitably performed at temperatures of 400 to 600° C. in a gaseous atmosphere including oxygen, such as air or a mixed gas of air and nitrogen. Moreover, the calcination step may include calcination under inert gas atmosphere, such as nitrogen, before or after the calcination in a gaseous atmosphere including oxygen.

[Step (2)] A contact treatment with an aqueous solution including an amine and/or a quaternary ammonium compound is given to the crystals after calcination in the step (1). An amine that may be included in this aqueous solution can be a primary, secondary, or tertiary amine of aliphatic, alicyclic, or aromatic series, and two or more of them may be used in combination if necessary. The following formula (1) shows preferable example of the amine.

$$NR^1R^2R^3 \qquad (1)$$

wherein $R^1$, $R^2$, and $R^3$ represent hydrogen atom, an alkyl group, or an allyl group, respectively, but $R^1$, $R^2$, and $R^3$ are not simultaneously hydrogen atom.

In the formula (1), when at least one of $R^1$, $R^2$, and $R^3$ is an alkyl group, examples of the alkyl group include methyl group, ethyl group, propyl group, butyl group, etc., and a carbon number thereof is usually approximately 1 to 4.

Examples of amines shown by the formula (1) include: alkylamines such as monomethylamine, monoethylamine, monopropylamine, monobutylamine, dimethylamine, diethylamine, dipropylamine, dibutylamine, trimethylamine, triethylamine, tripropylamine, and tributylamine; and allylamines such as monoallylamine, diallylamine, and triallylamine.

A quaternary ammonium compound that may be included in the aqueous solution can be, for example, a hydroxide, a halide, a sulfate, or a nitrate of quaternary ammonium, and two or more of them may be used in combination if necessary. Typical examples of the quaternary ammonium may be represented by the following formula (2):

$$R^4R^5R^6R^7N^+ \qquad (2)$$

wherein $R^4$, $R^5$, $R^6$, and $R^7$ represent an alkyl group, an aralkyl group, an aryl group, or an allyl group, respectively.

In the formula (2), when at least one of $R^4$, $R^5$, $R^6$, and $R^7$ is an alkyl group, examples of the alkyl group include methyl group, ethyl group, propyl group, butyl group, etc., and a carbon number thereof is usually approximately 1 to 4. When at least one of $R^4$, $R^5$, $R^6$, and $R^7$ is an aralkyl group, examples of the aralkyl group include benzyl, tolylmethyl group, etc., and a carbon number thereof is usually approximately 7 to 10. When at least one of $R^4$, $R^5$, $R^6$, and $R^7$ is an aryl group, examples of the aryl group include phenyl group, tolyl group, etc., and a carbon number thereof is usually approximately 6 to 10.

Examples of quaternary ammonium represented by the formula (2) include tetramethylammonium, tetraethylammonium, tetrapropylammonium, tetrabutylammonium, tributylbenzylammonium, propyltrimethylammonium, dibenzyldimethylammonium, tetraallylammonium.

Examples of quaternary ammonium other than those represented by the formula (2) include 4,4'-trimethylene bis(dimethylpiperidinium), 1,1'-butylene bis(4-aza-1-azonia bicyclo[2,2,2]octane), trimethyl adamantyl ammonium etc.

A concentration of the amine and/or quaternary ammonium compound included in the aqueous solution is usually 0.01 to 40% by weight as a total amount concentration thereof, and preferably 3 to 20% by weight. The preferable aqueous solution is an aqueous solution including a quaternary ammonium compound, and the more preferabe aqueous solution is an aqueous solution including a quaternary ammonium hydroxide. In addition, the aqueous solution may also include components other than the amine and quaternary ammonium compound, if necessary, and, for example, may also include other basic compounds such as sodium hydroxide or potassium hydroxide, in order to adjust hydroxide ion concentration in the aqueous solution.

The contact treatment with the aqueous solution may be performed by either of a batch process, or a continuous process. For example, the crystals may be immersed in the aqueous solution with agitation in a mixing vessel, or the aqueous solution may be flown through a tubular container filled with the crystals.

A temperature of the contact treatment is adjusted appropriately and is usually not more than 170° C. From the viewpoint of catalytic activity of the zeolite obtained, the temperature is not more than 100° C. The temperature is usually not less than 50° C., and preferably 60 to 100° C. A period time of the contact treatment is usually 0.1 to 100 hours. An amount of the aqueous solution to be used is usually 80 to 5000 parts by weight to the crystals 100 parts by weight.

The crystals after subjected to contact treatment by the step (2) are subjected to treatments of washing, drying, etc., if necessary, and then is calcined again [step (3)]. In the same manner as in the calcination of the above-mentioned step (1), this calcination step is usually suitably performed at temperatures of 400 to 600° C. in a gaseous atmosphere including oxygen, such as air or a mixed gas of air and nitrogen. Moreover, before or after the calcination in a gaseous atmosphere including oxygen, calcination under inert gas atmosphere, such as nitrogen, may be performed.

[Step (4)] Subsequently, a contact treatment with an aqueous solution including ammonia and/or an ammonium salt is given to the crystals after calcination in the step (3). An ammonium salt as used herein is a salt of ammonia, and for example, ammonium chloride, ammonium sulfate, ammonium nitrate, etc. may be mentioned.

A concentration of ammonia and/or an ammonium salt included in the aqueous solution is usually adjusted to give a pH of the aqueous solution of not less than 9, and preferably 9 to 13. Moreover, the aqueous solution may also include components other than the ammonia and ammonium salt, if necessary, and, for example, may also include amines and quaternary ammonium compounds previously illustrated as components in the aqueous solution used in the step (2).

The contact treatment with the aqueous solution may be performed by either of a batch process, and a continuous process, as the contact treatment in the step (2). For example, the crystals may be immersed in the aqueous solution with agitation in a mixing vessel, or the aqueous solution may be flown through a tubular container filled with the crystals.

A temperature of the contact treatment is usually 50 to 250° C., preferably 50 to 200° C., and more preferably 60 to 150° C. A period of time of the contact treatment is usually 0.1 to 10 hours. An amount of the aqueous solution used is usually 100 to 5000 parts by weight to the crystals 100 parts by weight.

The crystals after the contact treatment are subjected to treatment of washing, drying, etc., if necessary. In addition, two or more times of the contact treatment by the aqueous solution may be given, if necessary.

The zeolite manufactured by above step (1) to (4) may be used as a catalyst for organic synthesis reactions, and furthermore for various applications. Especially, it may advantageously be used as a catalyst for manufacturing ε-caprolactam by Beckmann rearrangement reaction of cyclohexanone oxime in a gaseous phase.

The zeolite as a catalyst may be molded for use according to a reactor to be used. As molding methods, for example, a method of molding by compression of a solid, a method of drying by spray of slurry, etc. may be mentioned. And, contact treating with steam can improve strength of a molded catalyst. Moreover, this catalyst may substantially consist only of a zeolite, and may also be a zeolite currently supported on a carrier.

As reaction conditions for Beckmann rearrangement, a reaction temperature is usually 250 to 500° C., and preferably 300 to 450° C. A reaction pressure is usually 0.005 to 0.5 MPa, and preferably 0.005 to 0.2 MPa. This reaction may be performed either in a fixed bed system, or in a fluidized bed system. A rate of feed of cyclohexanone oxime as a raw material is usually 0.1 to 20 $h^{-1}$, and preferably 0.2 to 10 $h^{-1}$, as a feeding rate of it (kg/h) per 1 kg of catalysts, that is, as a space velocity WHSV ($h^{-1}$).

Cyclohexanone oxime may, for example, either be independently introduced into a reaction system, or may be introduced together with inert gas, such as nitrogen, argon, and carbon dioxide. In addition, following methods are also effective, that is: a method by coexistence of ethers described in Japanese Patent Laid-Open Publication No. 2-250866; a method by coexistence of lower alcohols described in Japanese Patent Laid-Open Publication No. 2-275850; a method by coexistence of alcohols and/or ethers, and water described in Japanese Patent Laid-Open Publication No. 5-201965; a method by coexistence of ammonia described in Japanese Patent Laid-Open Publication No. 5-201966; and a method by coexistence of methylamine described in Japanese Patent Laid-Open Publication No. 6-107627.

The reaction may be carried out in combination with an operation of calcining the catalyst under gaseous atmosphere including oxygen, such as air. This calcining treatment of the catalyst enables removing by combustion of carbonaceous materials deposited on the catalyst, and can increase a conversion of the cyclohexanone oxime, and persistency of selectivity of the ε-caprolactam. For example, when reacting in a fixed bed system, a method is suitably adopted wherein cyclohexanone oxime is supplied, if necessary with other components to be reacted, into a fixed bed type reactor having a solid catalyst charged therein, subsequently supply of cyclohexanone oxime is stopped, then calcination is carried out by supplying a gas including oxygen, and furthermore these reaction and calcination are repeated. When reacting in a fluidized bed system, a method is suitably adopted wherein while cyclohexanone oxime is supplied, if necessary with other components to be reacted, into a fluidized bed reactor having a solid catalyst being fluidized therein and the reaction is conducted, the solid catalyst is extracted continuously or intermittently from the reactor, and the solid catalyst is returned into the reactor again after calcined in a calcination furnace.

As after-treatment operations of the reaction mixture obtained by the reaction, publicly known methods are appropriately employable, and for example, after cooling and condensation of the reaction generated gas, operations of extraction, distillation, crystallization, etc. are performed to separate ε-caprolactam.

EXAMPLES

Hereinafter, Examples of the present invention will be described, however, the present invention is not limited by them. In addition, a space velocity WHSV of cyclohexanone oxime ($h^{-1}$) was calculated by dividing a feeding rate (g/h) of cyclohexanone oxime by a catalyst weight (g). Analysis of cyclohexanone oxime and ε-caprolactam was conducted using a gas chromatography, a conversion of cyclohexanone oxime and a selectivity of ε-caprolactam were calculated by following equations, respectively, where, a number of moles of supplied cyclohexanone oxime was defined as X, a number of moles of unreacted cyclohexanone oxime as Y, and a number of moles of formed ε-caprolactam as Z.

a conversion of cyclohexanone oxime (%)=[(X-Y)/X]×100
a selectivity of ε-caprolactam (%)=[Z/(X-Y)]×100

Example 1

(a) Manufacture of Zeolite

[Hydrothermal synthesis]

Into an autoclave made of stainless steel, were added tetraethylorthosilicate [$Si(OC_2H_5)_4$] 100 g, 40% by weight tetra-n-propylammonium hydroxide aqueous solution 57.4 g, 48% by weight potassium hydroxide aqueous solution 0.36 g, and water 279 g. After hard agitation for 120 minutes at a room temperature, the mixture was further agitated at 105° C. for 36 hours, thus performing hydrothermal synthesis reaction. Obtained reaction mixture was filtered, and after filtrated residue was washed continuously using ion exchanged water until it gave a pH value of washing liquid of approximately 9, it was dried at a temperature of not less than 100° C.

[Step (1)]

After the obtained crystals were calcined for 1 hour in nitrogen at 530° C., they were further calcined for 1 hour in air at 530° C. to obtain powdered white crystals. A result of analysis by powder X-ray diffraction identified these powdered white crystals to be an MFI zeolite.

[Step (2)]

The calcined crystals 180 g were introduced into a beaker, and 22.5% by weight tetra-n-propylammonium hydroxide aqueous solution 165 g was added thereto. After agitation at 130° C. for 72 hours, crystals were separated by filtration, and washed and dried.

[Step (3)]

After the obtained crystals were calcined for 1 hour in nitrogen at 530° C., they were further calcined for 1 hour in air at 530° C. to obtain powdered white crystals.

[Step (4)]

The calcined crystals 8.8 g were introduced into an autoclave, and then a mixed liquor (pH 11.5) of 7.5% by weight ammonium nitrate aqueous solution 96 g and 25% by weight aqueous ammonia solution 147 g were added thereto. The crystals were separated by filtration after agitation of 1 hour at 90° C. A treatment by using a same mixed liquor of ammonium nitrate aqueous solution and aqueous ammonia solution described above was further given twice to the crystals, and subsequently, washing with water and drying were performed. Thus obtained zeolite was used as a catalyst in following (b).

(b) Manufacture of ε-Caprolactam

The zeolite 0.375 g obtained above (a) was charged into a tubular reactor made of quartz glass having an inner diameter of 1 cm to form a catalyst layer. The catalyst layer was beforehand heat-treated at 350° C. in nitrogen of 4.2 L/h for 1 hour. Subsequently, after lowering a temperature of the catalyst layer to 329° C. in nitrogen of 4.2 L/h, a mixture of vaporized cyclohexanone oxime/methanol=1/1.8 (weight ratio) was supplied to the tubular reactor at a feeding rate of 8.4 g/h (WHSV=8 $h^{-1}$ of cyclohexanone oxime) to be reacted. A reactive gas after 5.5 hour to 5.75 hour from a start of the reaction was sampled, and was analyzed using gas chromatography. A conversion of cyclohexanone oxime gave 99.8%, and a selectivity of ε-caprolactam gave 96.2%.

Comparative Example 1

In Example 1 (a), a same operation was performed except for not having performed step (4). The obtained crystals were used as a catalyst and reacted in a same manner as in Example 1 (b). A conversion of cyclohexanone oxime gave 69.3%, and a selectivity of ε-caprolactam gave 8.8%.

Comparative Example 2

In Example 1 (a), a same operation was performed except for not having performed step (2). The obtained crystals were used as a catalyst and reacted in a same manner as in Example 1 (b). A conversion of cyclohexanone oxime gave 99.5%, and a selectivity of ε-caprolactam gave 97.0%.

Example 2

A same operation as in Example 1 (a) was performed except that in the step (2) of Example 1 (a) an amount of the crystals after calcination was replaced by 20 g, instead of 22.5% by weight tetra-n-propylammonium hydroxide aqueous solution 165 g, 19% by weight tetra-n-propylammonium hydroxide aqueous solution 50 g was used, and instead of agitating at 130° C. for 72 hours, the mixture was agitated at 85° C. for 2 hours. The obtained crystals were used as a catalyst and reacted in a same manner as in Example 1 (b). A conversion of cyclohexanone oxime gave 100%, and a selectivity of ε-caprolactam gave 96.9%.

What is claimed is:

1. A method for manufacturing a zeolite comprising following steps of:
   (1): calcining crystals obtained by hydrothermal synthesis reaction of a silicon compound;
   (2): contact treating a calcined product obtained by the step (1) with an aqueous solution including an amine and/or a quaternary ammonium compound;
   (3): calcining a treated product obtained by the step (2); and
   (4): contact treating the calcined product obtained by the step (3) with an aqueous solution including ammonia and/or an ammonium salt.

2. The method for manufacturing a zeolite according to claim 1, wherein the zeolite is a pentasil type zeolite.

3. The method for manufacturing a zeolite according to claim 1, wherein the aqueous solution used in the step (2) is an aqueous solution including a quaternary ammonium hydroxide.

4. The method for manufacturing a zeolite according to claim 1, wherein a temperature of the contact treating in the step (2) is not more than 100° C.

5. A method for manufacturing ε-caprolactam wherein the ε-caprolactam is manufactured by Beckmann rearrangement reaction of cyclohexanone oxime in a gaseous phase in the presence of the zeolite manufactured by the method according to claim 1.

* * * * *